(12) United States Patent
Biesbrouck (10) Patent No.: US 9,993,816 B2
(45) Date of Patent: *Jun. 12, 2018

(54) APPARATUS AND METHOD FOR SEPARATING AND ANALYZING BLOOD

(75) Inventor: Gerardus Majella Biesbrouck, Santpoort Zuid (NL)

(73) Assignee: FABPULOUS B.V., Maastricht (NL)

( * ) Notice: Subject to any disclaimer, the term of this patent is extended or adjusted under 35 U.S.C. 154(b) by 1420 days.

This patent is subject to a terminal disclaimer.

(21) Appl. No.: 12/526,394

(22) PCT Filed: Feb. 8, 2008

(86) PCT No.: PCT/NL2008/050072
§ 371 (c)(1),
(2), (4) Date: Sep. 24, 2010

(87) PCT Pub. No.: WO2008/097091
PCT Pub. Date: Aug. 14, 2008

(65) Prior Publication Data
US 2011/0008908 A1    Jan. 13, 2011

(30) Foreign Application Priority Data
Feb. 9, 2007 (NL) ..................... 1033365

(51) Int. Cl.
*G01N 33/00* (2006.01)
*B01L 3/00* (2006.01)
*G01N 33/49* (2006.01)

(52) U.S. Cl.
CPC ............ *B01L 3/502* (2013.01); *G01N 33/491* (2013.01); *B01L 3/5021* (2013.01); *B01L 2200/16* (2013.01); *B01L 2300/0663* (2013.01); *B01L 2300/0681* (2013.01); *B01L 2400/0478* (2013.01)

(58) Field of Classification Search
None
See application file for complete search history.

(56) References Cited

U.S. PATENT DOCUMENTS

| | | | |
|---|---|---|---|
| 3,481,477 A * | 12/1969 | Farr | 210/359 |
| 3,931,018 A * | 1/1976 | North, Jr. | 210/359 |
| 4,256,693 A | 3/1981 | Kondo et al. | |
| 4,458,020 A * | 7/1984 | Bohn | B01L 3/502 422/400 |
| 4,477,575 A | 10/1984 | Vogel et al. | |
| 4,918,025 A | 4/1990 | Grenner | |
| 5,830,352 A * | 11/1998 | Holm | B01D 21/2405 137/605 |
| 6,171,870 B1 | 1/2001 | Freitag | |
| 6,280,400 B1 | 8/2001 | Niermann | |
| 6,375,817 B1 * | 4/2002 | Taylor | B01L 3/502784 204/453 |
| 6,632,681 B1 * | 10/2003 | Chu | A61B 10/0045 422/502 |
| 7,368,247 B2 | 5/2008 | Hochstrasser et al. | |
| 7,497,997 B2 * | 3/2009 | Glezer et al. | 422/504 |
| 7,745,228 B2 | 6/2010 | Schwind et al. | |
| 7,816,124 B2 | 10/2010 | Samsoondar | |
| 7,932,099 B2 * | 4/2011 | Egan et al. | 436/514 |
| 9,327,284 B2 * | 5/2016 | Rosman | B01L 3/5029 |
| 2002/0119147 A1 | 8/2002 | Howell et al. | |
| 2002/0160428 A1 | 10/2002 | Sundrehagen | |
| 2003/0064386 A1 * | 4/2003 | Karaki | G01N 33/54313 435/6.11 |
| 2003/0108447 A1 * | 6/2003 | Yokoi | B01L 3/5021 422/415 |
| 2003/0175167 A1 | 9/2003 | Takarori et al. | |
| 2004/0014157 A1 | 1/2004 | Sommer et al. | |
| 2004/0021469 A1 * | 2/2004 | Blomberg | G01N 33/491 324/434 |
| 2005/0059921 A1 | 3/2005 | Tu et al. | |
| 2005/0202513 A1 | 9/2005 | Kitayama et al. | |
| 2005/0232813 A1 | 10/2005 | Karmali | |
| 2005/0274672 A1 | 12/2005 | Tu et al. | |
| 2006/0063180 A1 * | 3/2006 | Yamashita | C12N 15/1006 435/6.16 |
| 2007/0031283 A1 * | 2/2007 | Davis et al. | 422/58 |
| 2007/0092509 A1 | 4/2007 | Mittra et al. | |
| 2007/0178009 A1 * | 8/2007 | Sakaino | A61B 5/14532 422/400 |

(Continued)

FOREIGN PATENT DOCUMENTS

| | | |
|---|---|---|
| CN | 1952664 | 4/2007 |
| DE | 29 22 958 | 12/1979 |

(Continued)

OTHER PUBLICATIONS

International Search Report of corresponding PCT, Application No. PCT/NL2008/050072, filed Feb. 8, 2008.
International Preliminary Report on Patentability and Written Opinion for PCT/NL2008/050072, dated Aug. 11, 2009, 7 pages.
International Search Report for PCT/NL2009/050260, dated on Sep. 8, 2009, 4 pages.
International Preliminary Report on Patentability and Written Opinion for PCT/NL2009/050260, dated Nov. 17, 2010, 8 pages.
Restriction Requirement in U.S. Appl. No. 12/992,262, dated Mar. 27, 2014, 9 pages.
Response to Restriction Requirement in U.S. Appl. No. 12/992,262, dated Sep. 22, 2014, 7 pages.

(Continued)

*Primary Examiner* — Ann Y Lam
(74) *Attorney, Agent, or Firm* — Morrison & Foerster LLP (57) ABSTRACT

An apparatus, comprising at least separating means (1) for separating blood plasma and red blood cells, which separating means (1) comprise pressure means (20) for pressing at least a part of the blood through a filter (26), wherein at least first collecting means (27) are provided for collecting separated blood plasma and at least one reagent is provided in said first collecting means (27) or can be introduced therein for reaction with substances or organisms present in said blood plasma.

24 Claims, 4 Drawing Sheets

(56) References Cited

U.S. PATENT DOCUMENTS

| | | |
|---|---|---|
| 2010/0311186 A1 | 12/2010 | Gregory et al. |
| 2011/0009796 A1 | 1/2011 | Tullis et al. |
| 2016/0103134 A1* | 4/2016 | Biesbrouck ...... G01N 33/54366 435/7.94 |

FOREIGN PATENT DOCUMENTS

| | | | | |
|---|---|---|---|---|
| EP | 0 508 010 | | 10/1992 | |
| EP | 0 550 950 | | 7/1993 | |
| EP | 1 152 241 | A2 | 11/2001 | |
| EP | 1 221 340 | A1 | 7/2002 | |
| EP | 1 346 773 | A2 | 9/2003 | |
| GB | 2 392 854 | A | 3/2004 | |
| GP | 2392854 | * | 9/2013 | ............. B01D 33/01 |
| JP | S54-178495 | | 12/1979 | |
| JP | S57-53661 | | 3/1982 | |
| JP | 2003-135435 | | 5/2003 | |
| JP | 2003-270239 | | 9/2003 | |
| JP | 2004-527760 | | 9/2004 | |
| JP | 2004-344874 | A | 12/2004 | |
| JP | 2003270239 | * | 3/2013 | ............. G01N 33/48 |
| RU | 2 358 267 | | 6/2009 | |
| WO | WO-86/00704 | | 1/1986 | |
| WO | WO 0240993 | * | 11/2001 | ............. G01N 33/49 |
| WO | WO 02/40993 | A1 | 5/2002 | |
| WO | WO-02/095409 | | 11/2002 | |
| WO | WO-03/083486 | | 10/2003 | |

OTHER PUBLICATIONS

Office Action for U.S. Appl. No. 12/992,262, dated Dec. 31, 2014, 15 pages.
Communication pursuant to Article 9493) EPC in EP 08712598.5, dated Oct. 5, 2016, 5 pages.

* cited by examiner

APPARATUS AND METHOD FOR SEPARATING AND ANALYZING BLOOD

This application is a national phase application of, and claims priority to, PCT/NL2008/050072, filed Feb. 8, 2008, which claims priority to Dutch Patent Application No. 1033365 filed Feb. 9, 2007, the disclosures of which are incorporated herein by reference.

The invention relates to an apparatus for separating and analyzing blood.

By blood analysis, deviations from a normal blood picture can be determined, from which, for instance, a pathological defect or a risk factor can be determined, at least it can be indicated that further examination thereof is advisable or necessary. Of course, a healthy blood picture may also be determined.

In US 2003/0175167 A1, an apparatus is described with which an amount of blood can be received in a chamber, the blood being diluted and then at least partly being pressed through a filter. The filter is chosen such that at least the blood plasma from the blood can pass this filter and is collected in a collecting space, while at least the red blood cells from the blood cannot pass the filter and remain behind in the chamber. Then a seal is provided in the passage between this chamber and the collecting space, so that the plasma cannot flow back. The apparatus is subsequently sent to a laboratory in order to carry out an analysis of the plasma. Here, it is particularly important that the separation between the plasma and the red blood cells is maintained, because otherwise, for instance, coagulation could occur, which makes the blood unusable for various tests afterwards. The analysis of the blood plasma is done by, for instance, spectral analysis.

US 2004/0133146 A1 describes an apparatus, where blood is sucked up with the aid of a thin tube, which blood is then supplied into a chamber, after which it is pressed against a filter with the aid of a piston, such that at least the blood plasma is forced through the filter and at least the red blood cells remain behind in the chamber. The separated blood plasma can then be examined, for instance with spectral analysis.

Compared to whole blood analysis, these apparatuses have the advantage that the blood does not need to be centrifuged. Thus, much less blood needs to be tapped and tests can be carried out more quickly.

These known apparatuses and the methods to be carried out therewith have the drawback that they still take up relatively much time before a test result is known to the patient whose blood has been tapped. This is because, although only little blood needs to be tapped and it does not need to be centrifuged anymore, the analysis needs to be carried out in a laboratory, so that, for sending and processing, relatively much time is needed. In addition, it can be experienced as a drawback by the patient that others get to know the results, even before the patient himself or herself.

GB 2 392 854 describes a filtration apparatus provided with a first chamber and a second chamber, mutually separated by a filter membrane. In one embodiment, this apparatus is described for the separation of blood into plasma and other blood components. In this embodiment, the second chamber is provided with a hollow plunger with the filter element at the leading end. Prior to use, in the second chamber, there are beads comprising reagent for a substance in the blood plasma. During use, the plunger is pressed into whole blood in the first chamber, so that blood plasma is forced through the filter into the second chamber. The beads dissolve in the blood plasma and react with the substance to be detected, so that a color change occurs as an indication of the presence of that substance. This test takes at least ten minutes.

EP 1 221 340 describes a universal testing apparatus in which different reagents can be provided, between or on filters. All kinds of liquids to be analyzed, such as whole blood, serum, foodstuffs and the like can be led along them for obtaining reactions. For use of serum, it is described that a gel with reagent can be provided between the filters. The filters then serve to clean the serum. Serum is separated from whole blood outside the apparatus and is introduced into the apparatus as such.

EP 1 152 241 describes an apparatus, in a series of embodiments, where at least three chambers are used for sequentially separating parts of whole blood, in order to collect blood plasma in a last chamber. Separation of different fractions of the blood is at least partly brought about by centrifugation.

U.S. Pat. No. 3,481,477 describes an apparatus for separating whole blood into serum and solid parts. To this end, a piston is provided in a tube, with the end of the piston being provided with a filter. Filter tablets can be provided for forming the filter. To the filter, a thin capillary tube is connected. During use, blood is introduced into the tube, after which the piston with the filter is pressed against the blood. Serum is forced by the filter tablets and is discharged via the capillary tube to a test tube or a reservoir formed in the inside of the piston. The filter tablets can contain a reagent for filtering components from the serum.

These known apparatuses have a complex structure and are complex to use and do not produce a desired quick, reliable result directly readable for a user.

Further, from for instance U.S. Pat. No. 4,477,575, an apparatus is known where use is made of reagents, where, on a test apparatus, a drop of blood is deposited, on top of a filter. Under the influence of capillary action and/or gravity, blood plasma is led through a filter layer while the red blood cells remain behind on the filter. In or near the filtering layer, a reagent is provided which can react with a component in the blood plasma. After that, a visual inspection of the reagent, at least the apparatus, can give a decisive answer about the presence or absence of this component in the blood. DE 29 22 958 furthermore describes multilayer filters with different reagents for different pathological or otherwise indicative factors in blood.

Such an apparatus offers the advantage that it can be carried out by a patient himself or herself or in his or her presence, so that the time for obtaining the test results can be reduced considerably. However, such tests also still require a few minutes or more, which is in many cases undesired. In addition, these tests have the drawback that they are very sensitive to, for instance, pollution from outside, since the apparatus is open, while, in addition, the degree of separation and consequently the amount of blood plasma obtained cannot be determined sufficiently accurately. Particularly when multilayer filters are used with different reagents, this drawback is increased further because it is unclear how much blood plasma ends up on which layer of the filter.

The invention contemplates providing an apparatus and/or method for analyzing blood.

The invention particularly contemplates providing a method and/or apparatus for relatively quickly separating at least blood plasma and red blood cells from whole blood and then analyzing at least the blood plasma.

A further object of the invention is providing a method and/or apparatus with which a user can carry out blood tests independently and relatively quickly.

The invention further contemplates providing an apparatus and/or method which enables separation and analysis of blood, where indications can be given of threshold values of one or more blood-related factors.

In a first embodiment, an apparatus according to the invention is characterized in that at least separating means for separating blood plasma and red blood cells are included, which separating means comprise pressure means for pressing at least a part of the blood through a filter, while at least first collecting means are provided for collecting separated blood plasma and at least one reagent which is provided in these first collection means or can be introduced therein for reaction with substances or organisms present in this blood plasma.

With such an apparatus, the advantage is achieved that at least blood plasma is separated under pressure from at least red blood cells, so that virtually instantaneously, the desired separation of blood plasma and red blood cells is obtained. In addition, at least the blood plasma is collected in collecting means in which the blood plasma directly comes or can be brought into contact with at least one reagent, so that, within a particularly short time, it can be determined whether a particular component in the blood of the respective is present, at least exceeds a particular value or limit. Preferably, use is made of reagents which allow visually determination of whether or not a respective reaction occurs, for instance by color change, structural change such as coagulation, dissolving, or the like.

The blood plasma is preferably collected in the first collecting means, designed as a space, separated from the environment, so that no pollution or leaking out of blood plasma can occur. Preferably, prior to use, in the apparatus, a known amount of diluent liquid is provided, in particular in above-mentioned chamber, while, in addition, a known amount of blood is introduced, so that the degree of dilution of the blood is always accurately known. Thus, accurate test results can be achieved quickly and simply.

In a first particularly advantageous embodiment, the at least one reagent is provided in the first collecting means, in particular on a wall part thereof. Preferably, this wall part is at least partly transparent so that change of, for instance, color or structure of the reagent is clearly visible from the outside of the apparatus, at least of the first collecting means, without these needing to be opened.

In an alternative embodiment, the at least one reagent is provided on an element or in an element which is or can be inserted into the first collecting means. This offers at least the advantage that the apparatus can have a substantially universal design, while, each time, a suitable reagent can be chosen, depending on the test to be carried out.

With an apparatus and method according to the invention, preferably, the reagent is chosen and/or dosed such that end point values can be determined, so that it can at least be seen whether a particular factor in the blood is above or below a preselected value.

In a particular embodiment, the apparatus is provided with a piston with which the blood, at least the blood plasma, can be pressed through a filter, while the first collecting means are preferably provided in the piston. The at least one reagent may then be provided on or in the piston.

In an apparatus and method according to the invention, each time, one reagent can be used, but combinations of reagents may also be provided, for simultaneously carrying out a series of tests. Thus, for instance, on a wall of the first collecting means, rings, surfaces or the like of different reagents may be provided. Optionally, of course, a reagent may also be provided in a different aggregation condition, for instance liquid or in the form of a solid.

In an alternative embodiment, the at least one reagent is provided in or on a separate holder, while the apparatus for separating the blood is provided with a pouring opening, particularly near the first collecting means, so that, after the blood plasma has been separated from the red blood cells, it can be poured into or on this holder, at least this at least one reagent.

The at least one reagent is preferably chosen from the group of reagents which only indicate presence of a substance or organism in the blood plasma and not a value for the concentration or the like. Preferably, the at least one reagent is therefore essentially binary: reaction of the reagent indicates, for instance by color change, coagulation or other transformation of the reagent, the blood plasma or a reaction between them, whether a particular threshold value is exceeded or not. For instance, a reagent which can indicate the presence of Helicobacter Pylori or a reagent which indicates an excess or limiting amount of coagulation factors. Also, reagents can be used which can indicate the presence of antigens, for instance a degree in which they are to be present or that a limit value is exceeded, for instance antigens with which the presence of tumors can be demonstrated or at least can be shown to be plausible. Also, reagents can be used with which the presence of, for instance, vitamins can be determined. Reagents can further be used with which, in case of exceeding or, conversely, falling short of a limit value, it can be indicated whether the exceeding is harmful to a patient. Such a reagent can advantageously be combined with a reagent which indicates exceeding or falling short of this limit value. Further, reagents can be used with which a therapeutic or non-therapeutic blood level can be determined, for instance of a medicine or toxic, for instance a medicine depending, for an optimal effect, on an optimal blood level or on a blood level which is not to be exceeded due to, for instance, undesired side effects. Combinations of reagents as mentioned may also be used. These reagents and uses are of course only mentioned by way of illustration and should not be taken as being limitative in any way.

By way of illustration of the invention, embodiments of an apparatus and method according to the invention will be explained in more detail with reference to the drawing, in which:

FIG. 4C schematically shows, in cross-sectional side elevational view, a filter for an apparatus according to FIG. 4;

In this description, same or corresponding parts are designated by same or corresponding reference numerals. Here, not all reference numerals are given in each of the drawings.

The embodiments shown and discussed all involve separation and analysis of blood. However, other biological samples may be tested with a same or similar apparatus. The embodiments of apparatuses and reagents given in the examples are only shown by way of illustration and should not be taken as being limitative in any way.

Figure 1:
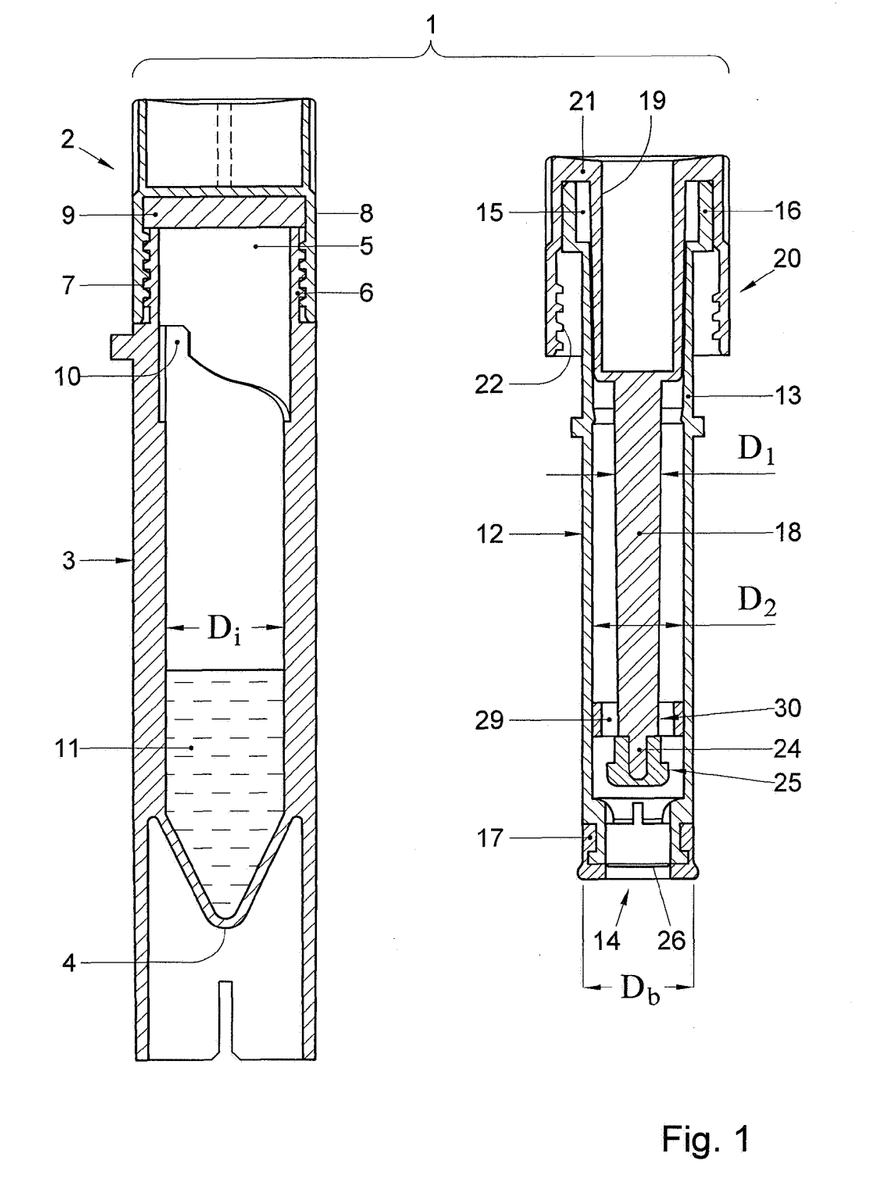
FIG. 1 shows, in cross-sectional view, prior to use, an apparatus according to the invention, in a first embodiment.

FIG. 1 shows, in partly cross-sectional side elevational view, an apparatus 1 according to the invention, in a first embodiment, in two parts. In FIG. 1, on the left side, a first part 2 is shown, formed by a transparent plastic casing 3, closed on a bottom side by a sharply tapering bottom 4 and open on the opposite side 5. The open side 5 is provided with a neck 6 with external screw thread 7 on which a cap 8 is screwed. The cap 8 clamps a gasket 9 on the neck 6, so that the inner space or chamber 10 within the casing 3 is closed off. In the chamber 10, a diluent liquid 11 is received, in a predetermined amount.

FIG. 1 shows, on the right side, second part 20 in the form of a piston part 12, comprising an at least partly transparent tubular part 13 with an open bottom end 14 and an opposite open top end 15, surrounded by a collar 16. Around the outside of the bottom end 14, a flexible ring 17 is provided with an outer diameter $D_b$ which matches the inner diameter $D_i$ of the casing 3 of the first part 2 in a manner to be described in more detail. In the tubular part 13, a trunk 18 is inserted, which has an outer diameter $d_1$ which is smaller than the inner diameter $d_2$ of the tubular part 13. On the top side of the trunk 18, a collar part 19 is provided which, on the top side, connects to an apron 21 extending outwards and is provided with an internal screw thread 22 which fits on the external screw thread 7 of the first part 2. The collar part sealingly fits into the top end 15, while the apron can abut the outside of the collar 16. The trunk 18 and the collar part 19 have such a length that, in the position shown in FIG. 1, the bottom end 24 of the trunk 18 is at some distance from the bottom end 14 within the tubular part 13. On the bottom end 24 of the trunk 18, a stop 25 is placed, which will further be explained.

In the bottom end 14 of the tubular part 13, a filter 26 is provided through which at least blood plasma can pass, but through which red blood cells cannot pass, at least with some dilution of the blood. Examples of filters and dilutions to be used are given in US 2003/1075167 A1, which are not to be taken as being limitative in any way.

Figure 2:
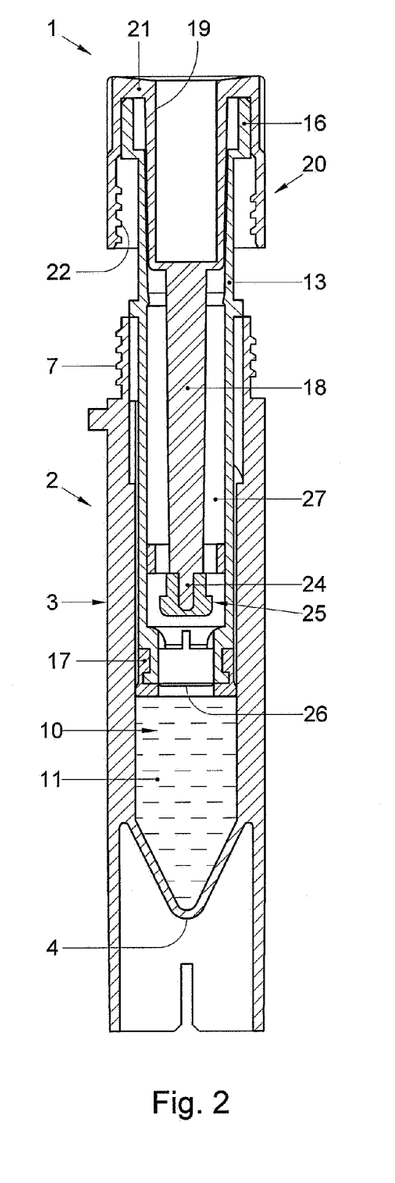
FIG. 2 shows, in partly retracted condition, an apparatus according to FIG. 1.

FIG. 2 shows the second part 20 in a condition where it is partly retracted into the first part 2, where a drop of blood with known volume is mixed into the diluent liquid. In this condition, the filter 26 lies on the diluted blood and the ring 17 seals against the inside of the casing 3. Thus, the chamber 10 is closed. From this position, the second part 20 can be pressed downwards further, in the direction of the bottom 4. Here, the filter 26 is forcefully pressed against the diluted blood, so that blood plasma is pressed upwards through the filter 26 while the red blood cells are stopped and remain behind in the chamber 10. Between the trunk 18, the tubular part 13, the filter 26 and the collar part 19, first collecting means 27 are formed, in the form of a ring chamber, in which the blood plasma is collected.

Figure 3:
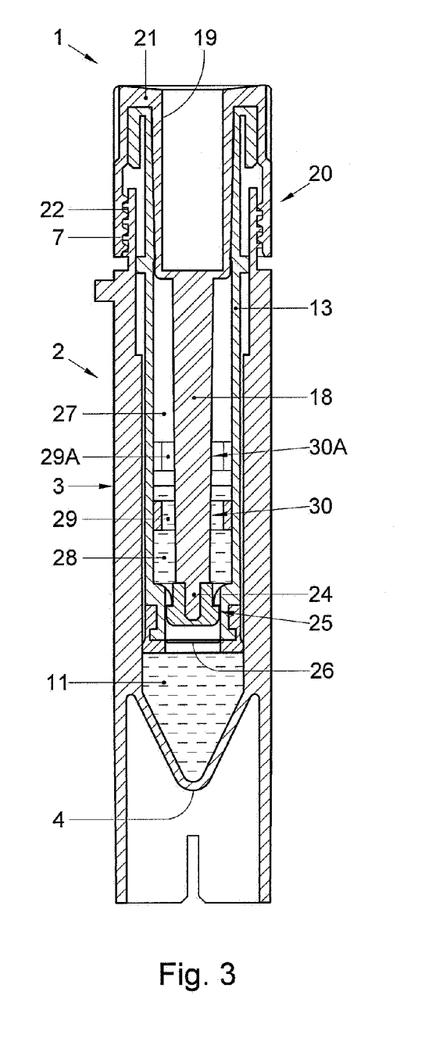
FIG. 3 shows, in wholly retracted condition, an apparatus according to FIGS. 1 and 2.

FIG. 3 shows, in cross-sectional side elevational view, an apparatus 1 according to the invention, where the second part 10 is completely pressed into the first part 2, so far that the internal screw thread 22 is screwed on the external screw thread 7 and the stop 25 closes off the open end of the tubular part 13 above the filter 26, so that the blood plasma 28 is prevented from flowing back from the first collecting means 27.

In the embodiment shown in FIGS. 1-3, on the inside of the tubular part 13, at least one surface 29 is provided which contains a reagent 30 for at least one element which is present, at least can be present, in the blood plasma 28. Preferably, the reagent 30 is provided as a ring-shaped surface, so that it is visible from the outside from all sides of the assembled apparatus 1. This allows reaction of the reagent 30 with above-mentioned element to be observed clearly, for instance due to color change, structural change, clotting, dissolving, or the like, if this element is present to a particular degree in the blood plasma. It will be clear that the reagent 30 or reagents can be chosen on the basis of the elements whose presence, concentration, level or the like needs to be determined. If desired, two or more surfaces 29, 29A, 29B, 29 . . . may be provided, with the same reagent but preferably with different reagents 30A, 30B, 30 . . . .

Figure 6:
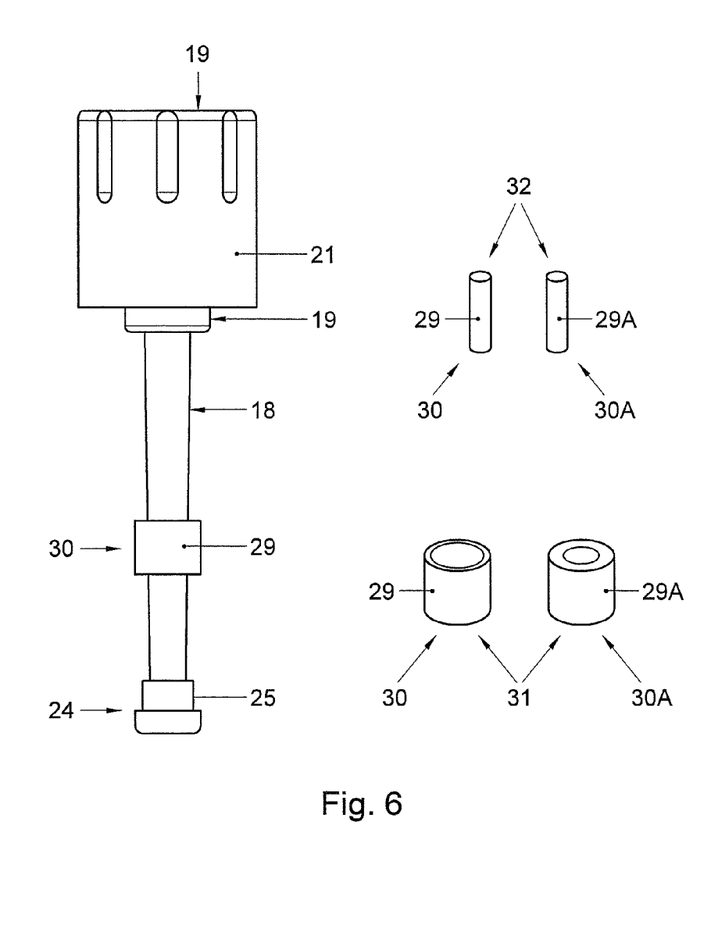
FIG. 6 shows, in side elevational view, a trunk of an apparatus according to FIG. 1, in an alternative embodiment.

In an alternative embodiment shown in FIG. 6, the reagent is provided on the trunk 18 in the form of a ring-shaped surface 29. Thus, the advantage is achieved that the trunk 18 can be chosen, for instance from a set of trunks 18 with different reagents, depending on the desired elements to be determined. Incidentally, this may of course also be achieved with different tubular elements 13 with different reagents.

In an alternative embodiment, an apparatus according to the invention may be supplied with a series of insertion elements such as (hollows) rods 31, rings 32 or the like as schematically shown in FIG. 6, where the different insertion elements carry different reagents 30, 30A, 30 . . . . Thus, each time, depending on the desired test, a suitable reagent or combination of reagents can be provided in the tubular element 13. Ring-shaped elements can then, for instance, be slid around the trunk 18 for forming a trunk 18 as shown in FIG. 6. Rods or the like may, for instance be placed in openings or slots in the trunk 18 or in a jacket or chamber enclosing the or each trunk, such as a space 27 or a tube 13, for instance loosely inserted.

Figure 5:
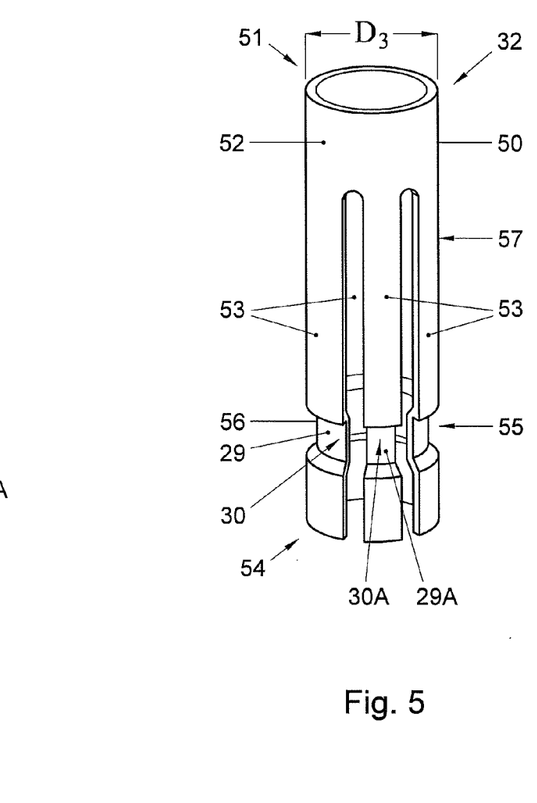
FIG. 5 schematically shows an insertion element for use with an apparatus according to the invention.

FIG. 5 schematically shows, in perspective view, an alternative embodiment of an insertion element 32 for use in an apparatus according to FIGS. 1-3. This insertion element 32 is substantially formed by a hollow cylindrical body 50, which comprises a ring-shaped portion 52 at a first end 51, from which a number of fingers 53 extend, in the direction of an opposite second end 54. Near this second end 54, the fingers 53 have a reduction 55 in that a portion 56 of each finger is offset inwards with respect to an outer surface 57 of above-mentioned body 50. On the outwardly facing surface 29 of the reduction 55, on each finger 53, a reagent 30 is provided. This may be the same reagent on each finger, but also, on different fingers 53, different reagents 30, 30A, 30 . . . may be provided, for instance for carrying out different, related or unrelated tests. The cylindrical body 50 has an outer diameter $D_3$ which is approximately equal to the inner diameter $D_2$ of the body 13, so that it can be retracted into the body 13 from the top end 15, preferably with the fingers 53 in the direction of the end 14. The outer surface 57 can then abut the inside of the body 13, while the surface 29 is kept at a distance therefrom. This allows the reagent 30, 30A, 30 . . . to properly come into contact with plasma collected in the space 27. Of course, the reagent may also be provided in a different manner, for instance directly on the surface 57, if it is kept at a distance from the wall of the body 13, or on an inwardly facing surface of the insertion part 32, in which case it is advantageous when at least the fingers 53 are at least partly transparent at the height of the reagent 30.

In this description, reagent or reagents or similar terms are also at least understood to mean antibodies or enzymes, which means that tests can be applied which are based on antibodies or enzymes.

Different reagents and other markers may be used, such as for instance antigens, chemical reagents, enzymes, chemical markers and the like. Reagents and markers may, for instance, be used for indicating problems with a heart, liver, kidney or other organs, glucose abnormalities such as diabetes, cholesterol abnormalities, abnormalities in one or more hormones, blood values in general and the like, viral or bacterial abnormalities such as influenza, malaria, hepatitis, HIV, inflammations, MS, ME and other indicators, in particular for existing health problems and/or health problems possibly to be expected. Herein, abnormalities are understood to mean such deviations from values normally expected for a respective person that, for a doctor, these would be or should be a reason to carry out further examinations or to intervene by, for instance, administering medicines, liquids, nutrients or to intervene surgically.

Examples of reagents 30, to which the invention is by no means limited, are for instance antibodies for HTLV I and/or II, cystatin C or similar markers for kidney functions or heart functions such as cardiovascular problems, heart infarcts ((myocardial) infarct) and/or heart attack (stroke), monoclonal antibodies, coagulation reagents such as lupus anticoagulant-sensitive or insensitive reagents, PSA antigen, HBS-1, HLA antibodies, HbA(1c) or GlyHb in hemoglobin measurement.

In a first example of an embodiment, on the inside of the tubular part 13, a surface 29 of cholesterol reagent, CHOD-Pap, Boehringer-Mannheim GmbH is provided as a reagent 30, which reagent 30 is suitable for demonstrating cholesterol (total cholesterol, HDL or LDL). In the chamber 10, 220 microliters of diluent liquid (buffer) were provided, after which 60 microliters of blood were diluted therein. By pressing down the second part into the first part, as described, in the first space 27, 220 microliters of blood plasma were collected. This blood plasma was brought into contact with the reagent by agitation (horizontal rocking), so that the reagent changed color from a neutral color to a characteristic color, in this case red, clearly visible from the outside. It was thus found that the cholesterol level in the blood was higher than a threshold value of 6.5 mmol/l. Control measurements of the whole blood taken via a venous blood sample and tested in laboratory demonstrated that the blood indeed had a value above that threshold value.

Figure 4A:
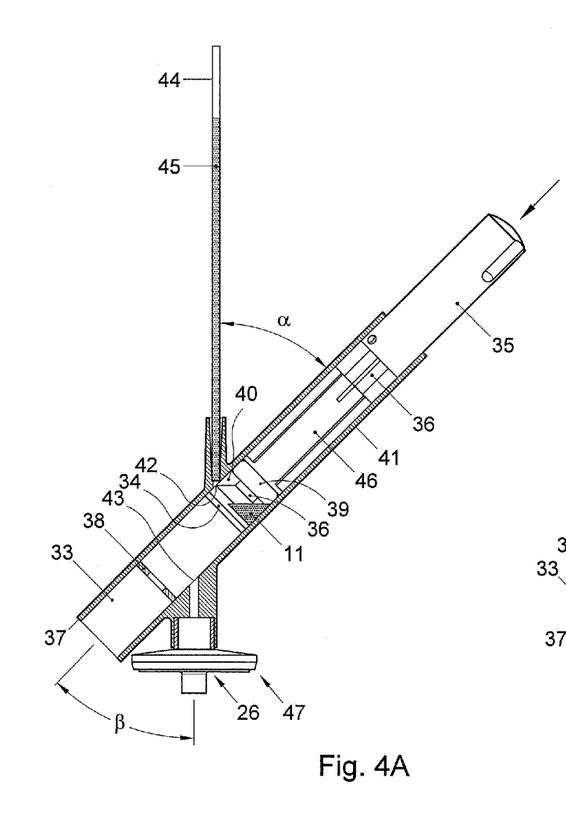
FIGS. 4A and B show, in partly cross-sectional side elevational view, an alternative embodiment of an apparatus according to the invention, in a starting position and an end position, respectively.
Figures 4B, 4C:
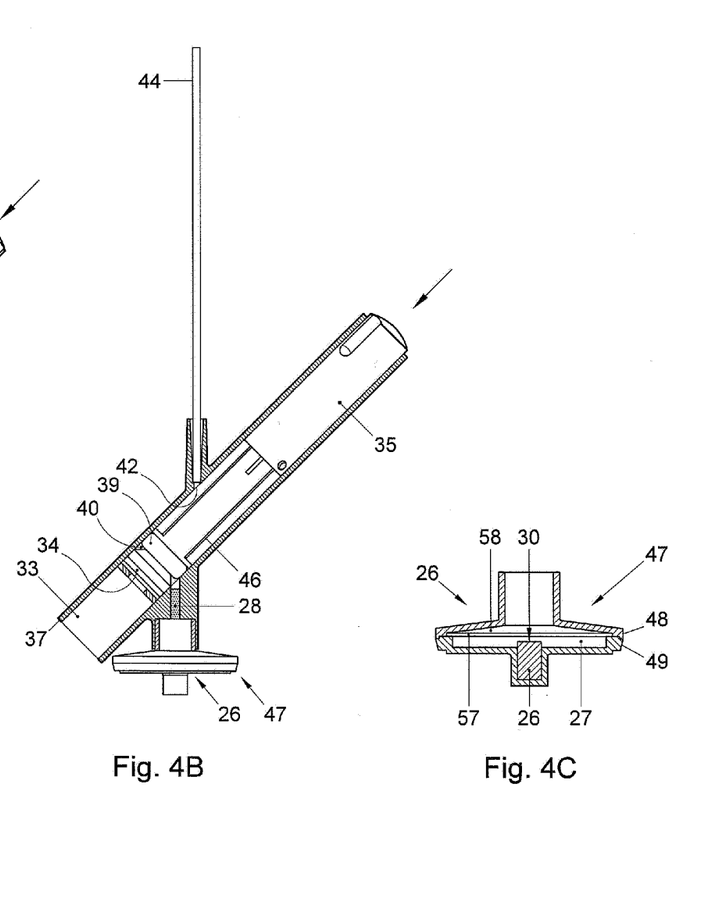

FIGS. 4A and B schematically show an apparatus 1 according to the invention, in an alternative embodiment, the basis of which is described in NL 1016646, which publication is understood to be incorporated herein by reference, at least with regard to the operation for separating plasma from blood.

This apparatus 1 comprises a hollow cylindrical body 33 in which a first piston 34 is sealingly movable with the aid of a pressure body 35 which, in a first position, rests against an end of the trunk 36 connected with the first piston and, in a second position, for instance rotated with respect to the first position through an angle of about 90 degrees about a longitudinal axis of the body 33, over the trunk 36. So, in the first position, the first piston 34 can be pressed in the direction of a bottom end 37 of the body 33 with the aid of the pressure body 35, up to against a stop 38. A second piston 39 with trunk 46 is provided around the trunk 36 and seals against both the trunk and the inside of the body 33. The second piston 39 is, for instance, a rubber ring. Between the first and the second piston 34, 39, a treatment space 40 is enclosed, the volume of which is variable. Therein, a treatment fluid or other material can be included, such as a buffer 11, for instance a phosphate buffer, similar to FIGS. 1-3.

In a wall 44 of the body 33, an inlet opening 42 and an outlet opening 43 are provided. A capillary 44 can be inserted into the inlet opening, so that the contents of the capillary 44 can be sucked into the body, between the two pistons 34, 39, in the treatment space 40, as will be discussed hereinbelow. To the outlet opening 43, a filter 26 connects, into which and/or through which at least the contents of the treatment space 40 can be forced.

In a starting position, shown in FIG. 4A, the pistons 34, 39 are relatively high in the body 33 and relatively close to each other. The inlet opening preferably opens just into the treatment space, which treatment space 40 has a relatively small volume. A capillary 44 filled with whole blood 45 as a sample is inserted into the inlet opening 42. By now pressing the first piston 34 in the direction of the bottom end 37 of the body, it passes the outlet opening 43 while, in addition, the volume of the treatment space 40 is increased, in that the second piston 39 will not or at least not completely follow the movement of the first piston 34 in a first part of the maximum stroke, i.e. the maximum distance over which the pressure body 35 can move from the starting position in the direction of the bottom end 37, before it is brought into the second position. Because the volume of the treatment space 40 increases, the contents of the capillary will be sucked into the treatment space and mix therein with the treatment fluid 11.

Then the pressure body is brought into the second position with respect to the trunk 36, so that it can be pressed further in the direction of the bottom end 37, over the trunk 36, thus pressing the second piston 39 is the direction of the first piston 34. The volume of the treatment chamber is thereby reduced back, in particular minimized, and the mixture of the treatment fluid and the sample is pressed through the outlet opening 43, into and/or through the filter 26. The filter may be any suitable filter, for instance a glass fiber filter. Here, plasma is separated from the blood, in that the plasma is pressed through the filter, with blood particles such as erythrocytes and leukocytes removed.

According to the invention, in and/or to the filter 26, at least one test surface 29 is provided as shown in FIG. 4C, formed by or comprising a reagent 30, such as for instance mentioned hereinabove. Because the plasma is forced through the filter, it directly and intensively comes into contact with the or each test surface 29 and consequently with the or each reagent 30, so that the test result can be read out virtually instantaneously. An advantage is that it does not need to be provided on an external reagent surface, so that pollution of the plasma and/or the reagent can be prevented. In addition, the plasma can be collected in the filter 26, at least the housing 47 thereof, so that pollution and in particular contamination of the environment can be prevented. This is particularly important in use of biological samples such as blood in which pathogenic elements may be present.

FIG. 4C schematically shows a filter 26 for an apparatus 1 according to FIGS. 4A and B, which filter 26 comprises a housing 47. The housing 47 is at least partly and preferably wholly transparent, such that the filter surface 48 or at least a part thereof on which reagent 30 is provided can be seen without the housing 47 needing to be opened. This prevents pollution of plasma, reagent and/or the environment. The housing 47 may, for instance, comprise two housing parts 48, 49 attached to each other enclosing a filter element 57 as described earlier, for separation of blood plasma and blood corpuscles. On a side operatively facing the outlet opening 43, in the first housing part 48, a chamber 58 is provided in which blood corpuscles remain behind, above the filter element 57. In the second housing part 49, a collecting space 27 is provided in which the separated plasma 28 is collected. In this space, at least one surface 29 is provided on which or in which a reagent can be included for reaction with the blood plasma. This surface 29 may, for instance, be provided on the filter element 57, on the side thereof facing the collecting space 27, while it may, for instance, have a porous design, so that intensive contact is obtained between plasma and reagent. The surface 29 may also, as shown in FIG. 4C, be provided on the inside of the housing 47, in the collecting space 27, or both. In this embodiment, the second housing part 49 has a transparent design, at least at the height of the surface 29, here provided on a block 59, so that, for instance, discoloration of the block as a result of the reaction between elements of or in the plasma and the or a reagent 30 is visible from outside the housing 47.

The invention is by no means limited to the embodiments given in the drawing and description. Many variations thereof are possible within the framework of the invention described by the claims.

Thus, with use of a filter, a housing can be used in which the plasma is at least partly collected, while the housing is at least partly transparent and the or each reagent is provided therein. This offers the advantage of good protection against pollution and/or contamination. In addition, the apparatus or at least the plasma collected therein can then be used for further tests. Thus, the apparatus as a whole or the filter and/or the housing may, for instance, be sent to a laboratory, where further tests can be carried out to, for instance, verify a first indication obtained with the or a reagent or to examine it further.

The invention claimed is:

1. An apparatus for separating blood plasma and red blood cells in a blood sample, said apparatus comprising:
   a) a separator comprising a filter and a pressurizer for pressing at least part of a blood sample through said filter to provide separated blood plasma and red blood cells, wherein blood plasma can pass said filter but red blood cells cannot; and
   b) a collector for collecting separated blood plasma, wherein at least one reagent is provided in said separator and/or said collector,
   wherein said at least one reagent does not contact said filter and does not contact any other filter during filtering, and
   wherein said at least one reagent is capable of reacting with a substance or an organism in said separated blood plasma.

2. The apparatus of claim 1, further comprising a chamber for introducing said blood sample into said apparatus.

3. The apparatus of claim 2, wherein said chamber comprising a diluent for said blood sample.

4. The apparatus of claim 2, wherein said filter is provided at or near the end of a tubular element which can be inserted into said chamber for pressing said blood sample through said filter, and wherein said collector is formed by an interior wall part of said tubular element.

5. The apparatus of claim 4, further comprising a piston that can be inserted into said tubular element, wherein said collector is formed between said piston and said interior wall part of said tubular element.

6. The apparatus of claim 5, wherein said piston comprises a stop element that, when said piston is inserted into said tubular element, engages said tubular element to prevent separated blood plasma from flowing out of said collector.

7. The apparatus of claim 5, wherein said at least one reagent is provided on said piston.

8. The apparatus of claim 4, wherein said at least one reagent is provided on an interior wall part of said tubular element, or in an insertion element which can be introduced into said collector.

9. The apparatus of claim 1, wherein said collector comprises at least an opening for pouring out separated blood plasma collected in said collector.

10. The apparatus of claim 1, wherein said at least one reagent is provided on a wall part of said collector, and the collector is a closed container for containing the separated out blood plasma separated from the environment of the apparatus.

11. The apparatus of claim 1, wherein said at least one reagent is provided in said separator and/or said collector as a liquid.

12. The apparatus of claim 1, wherein said at least one reagent is immobilized in said separator and/or said collector.

13. The apparatus of claim 1, wherein at least two different reagents are provided in said separator and/or said collector.

14. The apparatus of claim 13, wherein at least a first reagent is a reagent or marker for indicating a heart disease or condition, a liver disease or condition, a kidney disease or condition, a glucose abnormality, diabetes, a cholesterol abnormality, a hormone abnormality, a blood value, a viral infection, a bacterial infection, influenza, malaria, hepatitis, HIV, inflammation, multiple sclerosis, or myalgic encephalopathy, and
   wherein at least a second reagent is selected from the group consisting of an antibody for HTLV I, an antibody for HTLV II, cystatin C, a marker for kidney function, a marker for heart function, a marker for a cardiovascular disease or condition, a marker for heart infarction, a marker for myocardial infarction, a marker for heart attack, a marker for stroke, a monoclonal antibody, a coagulation reagent, a lupus anticoagulant-sensitive reagent, a lupus anticoagulant-insensitive reagent, PSA antigen, HBS-1, a HLA antibody, HbA (1c), GlyHb, and a marker for hemoglobin level.

15. The apparatus of claim 1, wherein said at least one reagent is selected from the group consisting of an antigen, a chemical reagent, an enzyme, and a chemical marker.

16. The apparatus of claim 1, wherein said collector is at least partially transparent, such that said at least one reagent is at least partially visible from the outside of said apparatus.

17. The apparatus of claim 1, wherein said separated blood plasma comprises a nondenaturized protein.

18. A method for analyzing a blood sample, comprising:
   providing an apparatus of claim 1;
   introducing a blood sample, diluted or undiluted, into said apparatus;
   separating blood plasma from red blood cells of said blood sample by engaging said separator of said apparatus;
   contacting said separated blood plasma with said at least one reagent, under conditions wherein a reaction occurs between said at least one reagent and said substance or organism; and
   detecting an indicator of said reaction.

19. The method of claim 18, wherein the indicator of said reaction can be observed from the outside of said collector.

20. The method of claim 18, wherein a preselected amount of said blood sample is introduced into said apparatus and mixed with a preselected amount of a diluent to obtain a desired dilution, whereafter said diluted blood sample is pressed against said filter, such that blood plasma is forced through said filter into said collector and red blood cells are held back by said filter to provide said separated blood plasma.

21. The method of claim 18, wherein said at least one reagent is a reagent or marker for indicating a heart disease or condition, a liver disease or condition, a kidney disease or condition, a glucose abnormality, diabetes, a cholesterol abnormality, a hormone abnormality, a blood value, a viral infection, a bacterial infection, influenza, malaria, hepatitis, HIV, inflammation, multiple sclerosis, or myalgic encephalopathy, or is selected from the group consisting of an antibody for HTLV I, an antibody for HTLV II, cystatin C, a marker for kidney function, a marker for heart function, a marker for a cardiovascular disease or condition, a marker for heart infarction, a marker for myocardial infarction, a marker for heart attack, a marker for stroke, a monoclonal antibody, a coagulation reagent, a lupus anticoagulant-sensitive reagent, a lupus anticoagulant-insensitive reagent, PSA antigen, HBS-1, a HLA antibody, HbA(1c), GlyHb, and a marker for hemoglobin level.

22. The method of claim 18, wherein at least two reagents are provided in said separator and/or said collector.

23. The apparatus of claim 1, wherein said at least one reagent is provided as a ring-shaped surface visible from the outside of said apparatus.

24. An apparatus for separating blood plasma and red blood cells in a blood sample, said apparatus comprising:
  a) a separator comprising a filter and a pressurizer for pressing at least part of a blood sample through said filter to provide separated blood plasma and red blood cells, wherein blood plasma can pass said filter but red blood cells cannot; and
  b) a collector for collecting separated blood plasma,
  wherein at least one reagent is provided in said separator and said collector, or provided in said collector,
  wherein said at least one reagent does not contact said filter,
  wherein said at least one reagent is capable of reacting with a substance or an organism in said separated blood plasma, and
  wherein said at least one reagent does not contact said filter and does not contact any other filter during filtering.

* * * * *